United States Patent
Lin et al.

(10) Patent No.: US 8,293,942 B2
(45) Date of Patent: Oct. 23, 2012

(54) REAGENTS AND METHOD FOR MEASURING HYDROXYL NUMBER IN POLYOLS

(75) Inventors: Chih-Chien Lin, Kaohsiung (TW); Chien-Tien Chen, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 514 days.

(21) Appl. No.: 12/107,247

(22) Filed: Apr. 22, 2008

(65) Prior Publication Data

US 2009/0105496 A1     Apr. 23, 2009

(30) Foreign Application Priority Data

Oct. 23, 2007 (TW) ............................... 96139630 A

(51) Int. Cl.
C07C 53/00 (2006.01)
(52) U.S. Cl. ..................................................... 562/887
(58) Field of Classification Search .................. None
See application file for complete search history.

(56) References Cited

U.S. PATENT DOCUMENTS

| | | | | |
|---|---|---|---|---|
| 5,600,011 A | * | 2/1997 | Kobayashi | 568/335 |
| 2006/0173213 A1 | * | 8/2006 | Chen | 562/887 |
| 2007/0017151 A1 | | 1/2007 | Chen | |

FOREIGN PATENT DOCUMENTS

| | | |
|---|---|---|
| CN | 101430308 | 5/2009 |
| JP | 07-077524 | 3/1995 |
| JP | 2003-043027 | 2/2003 |
| TW | I290953 | 12/2007 |

OTHER PUBLICATIONS

Choudary et al., Journal of Molecular Catalysis A: Chemical (1999), 140(1), 25-29.*
Chandrasekhar et al., Tetrahedron Letters 39 (1998) 3263-3266.*
Chen et al., Journal of Organic Chemistry 2005 70, p. 1188-1197; published on web Jan. 25, 2005.*
Chen et al., Organic Letters 2001, 3 (23) 3729-3732.*
Hachiya et al., Bull. Chem. Soc. Jpn., 68, 2053-2060 (1995).*
CN Office Action mailed Feb. 12, 2010.
"A Cylation Methods of Determing the Hydroxyl Value of Polyether"; Hu Yujuan et al.; Dec. 28, 2005 Polyurethane Industry, 2005, vol. 20, No. 6.
Taiwanese language office action dated Jan. 14, 2011.
Chinese language office action dated Dec. 31, 2010.
Choudary, B.M., et al.; "Vanadyl(IV) Acetate, A New Reusable Catalyst for Acetylation of Alcohols;" Journal of Molecular Catalysts A: Chemical 140; 1999; pp. 25-29.
Japanese language office action dated Aug. 30, 2011.
English language translation of office action.
English language translation of abstract of TW I290953 (published Dec. 11, 2007; pp. 13-14 of attachment).
Chen, C.T., et al.; "Nucleophilic Acyl Substitutions of Esters with Protic Nucleophiles Mediated by Amphoteric, Oxotitanium, and Vanadyl Species;" Journal of Organic Chemistry; 2005; pp. 1328-1339.
Japanese language Notice of Allowance dated Dec. 27, 2011.
English language translation of abstract of JP 07-077524 (published Mar. 20, 1995).
English language translation of abstract of JP 2003-043027 (published Feb. 13, 2003).
European Search Report dated Jan. 23, 2012.
English language translation of abstract of CN 101430308 (published May 13, 2009).
"Determination of Hydroxyl Content of Polyurethane Polyols and Other Alcohols" Wellons et al., Anal. Chem. 1980, 52, 1374-1376.
Japanese language office action dated Mar. 1, 2011.
English language translation of office action, Mar. 1, 2011.
Choudary, B.M., et al.; "Van Adyl (IV) Acetate, A New Reusable Catalyst for Acetylation of Alcohols;" J Mol Catal A Chem; Mar. 19, 1999; vol. 140; No. 1; pp. 25-29.

* cited by examiner

Primary Examiner — Karl J Puttlitz
(74) Attorney, Agent, or Firm — Thomas|Kayden

(57) ABSTRACT

A pyridine-free esterification reagent for anhydride method to determine the hydroxyl number of polyols is provided. The reagent includes an anhydride, an oxometallic complex having a formula of $MO_mL_n$, and a neutral or slightly acidic solvent, wherein M includes transition metals of IVB, VB, or VIB group, L includes (OTf), X,

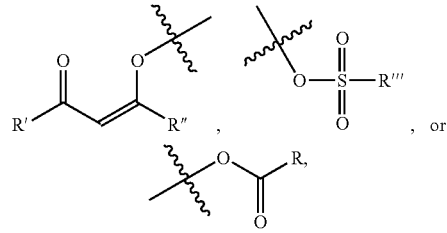

and m and n are an integer greater than or equal to 1, wherein X is halogen, and R, R', R", and R''', independently, are alkyl, aryl, or heterocyclic groups containing nitrogen, oxygen, phosphorus, or sulfur heteroatoms. The invention also provides a method to determine the hydroxyl number of polyols.

11 Claims, No Drawings

REAGENTS AND METHOD FOR MEASURING HYDROXYL NUMBER IN POLYOLS

BACKGROUND OF THE INVENTION

1. Field of the Invention

The invention relates to an esterification reagent with the anhydride method to determine the hydroxyl number in polyols, and more specially it relates the use of solvents in the absence of pyridine and having improved function.

2. Description of the Related Art

"Plastics-Polyols for use in the production of polyurethane-Determination of hydroxyl number" (ISO 14900:2001 (E)) describes the currently accepted acetic or phthalic anhydride methods for hydroxyl content determination of polyethers and polyesters. These methods which use pyridine to dissolve the hydroxy-containing samples is a serious disadvantage. Pyridine is toxic and odorous. It is harmful to your eyes, nose, throat, and skin, and is classified to an acute toxic substance (level 4) in the material hazard classification.

This method is based on the esterification of polymers bearing hydroxyl group(s) by anhydride in pyridine solution according to the following reaction scheme:

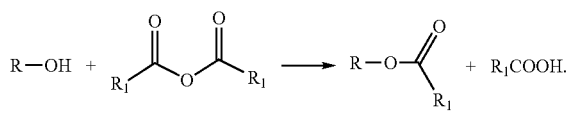

A test portion is refluxed in a solution of anhydride in pyridine to esterify the hydroxyl groups present. The reaction is catalyzed by imidazole. The excess anhydride reagent is hydrolyzed with water and the resulting acid is titrated with standardized sodium hydroxide solution. The hydroxyl content is calculated from the difference in titration of the test portion and a blank solution.

Here Pyridine serves as a sample solvent and a proton scavenger (*Anal. Chem.* 1980, 52, 1374-1376) in order to easily dissolve the sample so that the esterification reaction proceeds more smoothly in a quantitative conversion.

Since pyridine exhibiting a specific and unpleasant odor, analytical operations have been inconvenient. Therefore, solvent candidates that are free from pyridine odors have long been desired.

BRIEF SUMMARY OF THE INVENTION

One of embodiment of the invention is to provide an esterification reagent for anhydride method to determine the hydroxyl number of a given polyol. The reagent comprises an anhydride, an oxometallic complex having a formula of $MO_mL_n$ and a pyridine-free organic solvent, wherein M comprise transition metals of IVB, VB, or VIB group, L comprises (OTf),

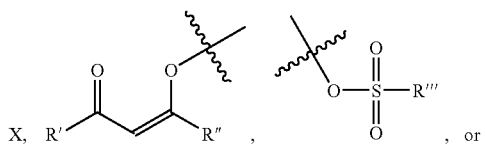

-continued

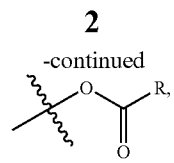

m and n are an integer greater than or equal to 1, wherein X is halogen, and R, R', R", and R''' independently are alkyl, aryl, or heterocyclic groups containing nitrogen, oxygen, phosphorus, or sulfur heteroatoms.

One embodiment of the invention provides a method for measuring hydroxyl number comprising mixing a given sample having hydroxyl group(s) and the disclosed reagent to prepare a solution. The solution is titrated with a sodium hydroxide solution until a titration end point is achieved, and the hydroxyl content value of the sample is calculated.

The hydroxyl groups of the sample is rapidly esterified with the anhydride catalyzed by an oxometallic complex at reflux temperature. Hydrolysis of the excess anhydride is done by quenching the solution with water. Neutralization of the resulting acid which appears during the esterification process and of the acid formed during the hydrolysis is done by addition of sodium hydroxide solution. The hydroxyl number for a given sample is thus obtained by calculation of the titration volume difference between the standardized sodium hydroxide solutions consumed by a blank and the test portion, respectively.

In the invention, a quantitative esterification between the anhydride and the hydroxyl groups in a given sample catalyzed by the oxometallic complex is performed in a dried solvent without pyridine to scavenge proton in order to measure the hydroxyl number of the polyol polymers.

Toxic and odorous pyridine is replaced by the neutral or acidic organic solvent, which effectively improve working environment and reduce toxic substance contamination.

A detailed description is given in the following embodiments.

DETAILED DESCRIPTION OF THE INVENTION

The following description is the best-contemplated mode of carrying out the invention. This description is made for the purpose of illustrating general principles of the invention and should not be taken in a limiting sense. The scope of the invention is best determined by reference to the appended claims.

One embodiment of the invention provides an esterification reagent for anhydride method to determine the hydroxyl number in a given polyol. The reagent recipe comprises an anhydride, an oxometallic complex having a formula of $MO_mL_n$, and a solvent.

In formula $MO_mL_n$, M may comprise transition metals of IVB, VB, or VIB group. L may comprise (OTf),

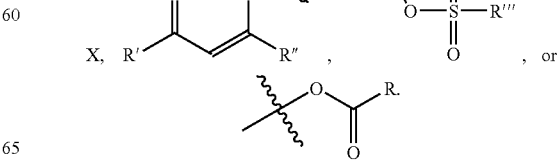

m and n may be an integer greater than or equal to 1. X may be halogen. R, R', R", and R'" may, independently, be alkyl, aryl, or heterocyclic groups containing nitrogen, oxygen, phosphorus, or sulfur heteroatoms.

The anhydride has formula $(RCO)_2O$. R may comprise acyclic aliphatic, cyclic aliphatic, haloaliphatic or heterocyclic groups, for example, methyl, trifluoromethyl, monochloromethyl, ethyl, propyl, or isopropyl. Mixtures of such anhydrides can also be used, as can other equivalents.

The solvent may comprise haloalkane solvents for example dichloromethane, chloroform or tetrachloromethane, aromatic solvents for example benzene, toluene, xylene, diethylbenzene or $C_1$-$C_5$ carboxylic acid. Such solvents can be used individually or in any desired ratio.

The oxometallic complexes may have various compositions. When M is the transition metals of IVB group, m is 1, n is 2, L may comprise (OTf),

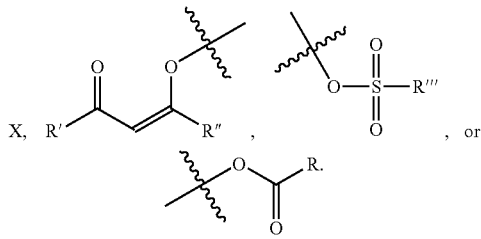

X may be halogen R, R', R", and R'" may, independently, be alkyl, aryl, or heterocyclic groups containing nitrogen, oxygen, phosphorus, or sulfur heteroatoms.

When M is the transition metals of VB group, m is 1, $L_n$ may comprise $(OTf)_2(THF)_2$, $(OTf)_2(THF)_3$, $Cl_2(THF)_2$, $Cl_2(THF)_3$, $(OAc)_2$, $(OTs)_2$, $(OSO_2Cl_2H_2)_2$, $(SO_3$-alkyl$)_2$, $(SO_3$-alkyl$)_2(THF)_2$ or $(SO_3$-alkyl$)_2(THF)_3$.

When M is the transition metals of VIB group, m is 1, n is 4, L may comprise X. X may be halogen.

When M is the transition metals of VIB group, m is 2, n is 2, L may comprise (OTf),

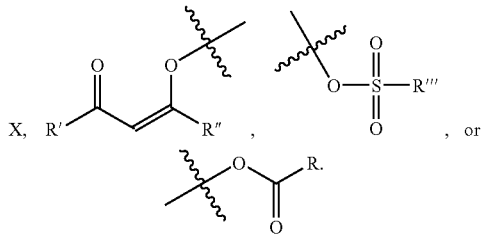

X may be halogen. R, R', R", and R'" may, independently, be alkyl, aryl, or heterocyclic groups containing nitrogen, oxygen, phosphorus, or sulfur heteroatoms.

In the reagent, the anhydride and the oxometallic complex have a molar ratio of about 100:10-100:0.01 or 100:5-100:0.2. The solvent and the anhydride have a weight ratio of about 10:1-1:1.

One embodiment of the invention provides a method for measuring hydroxyl number of a given polyol, which comprises the following steps. A sample bearing hydroxyl group(s) is mixed with the disclosed reagent to prepare a solution. The solution is then titrated with a sodium hydroxide solution until a titration end point as judged by phenolphthalein indicator is achieved. Finally, the hydroxyl number of the sample is calculated.

The hydroxyl groups of the sample is rapidly esterified with the anhydride catalyzed by an oxometallic complex at reflux temperature. The excess anhydride is hydrolyzed with water. Neutralization of the resulting acid which appears during the esterification process and of the acid formed during the hydrolysis is done by addition of sodium hydroxide solution. The hydroxyl number of the sample can thus be obtained by calculation of the titration volume difference between the two standardized sodium hydroxide solutions which are consumed by a blank and the test portion, respectively.

In the invention, a quantitative esterification between the anhydride and the hydroxyl groups containing sample catalyzed by the oxometallic complex is performed in a dried solvent without pyridine to scavenge proton in order to measure the hydroxyl number of the polyol polymers.

Toxic and odorous pyridine is replaced by the neutral or acidic organic solvent, which effectively improve working environment and reduce toxic substance contamination.

Example 1

Preparation of the Esterification Reagent for Measuring the Hydroxyl Number of a Given Polyol The reagent was prepared according to known methods with exclusion of atmospheric moisture and with reagent grade chemicals.

Esterification reagent A: 2.0 g $MoO_2(acac)_2$ (6mmol) was dissolved in 50 g acetic anhydride (490 mmol) with magnetic stirring at room temperature to prepare a solution. The solution was then transferred to a 100-mL volumetric flask. The solution was diluted to volume mark with toluene under adequately shaking. Reagent A was stored in a brown bottle.

Esterification reagent B: 1.3 g $VO(OAc)_2$ (6.6 mmol) was dissolved in 64 g propionic anhydride (492 mmol) with magnetic stirring at room temperature to prepare a solution. The solution was then transferred to a 100-mL volumetric flask. The solution was diluted to volume mark with xylene under adequately shaking. Reagent B was stored in a brown bottle.

Esterification reagent C: 1.3 g $VOCl_2$-$(THF)_3$ (6.6 mmol) was dissolved in 64 g propionic anhydride (492 mmol) with magnetic stirring at room temperature to prepare a solution. The solution was then transferred to a 100-mL volumetric flask. The solution was diluted to volume mark with xylene under adequately shaking. Reagent C was stored in a brown bottle Unless indicated otherwise herein all details of the titratimetric method to determinate the hydroxyl number of a given sample of this invention are fully conventional and disclosed, e.g., "Plastics-Polyols for use in the production of polyurethane-Determination of hydroxyl number" (ISO 14900:2001 (E)).

Esterification procedure: weight the test portion into a clean dry conical flask, then pipette 5 mL of the esterification reagent into each flask used for the test portion and a blank determination. Connect the flask to a condenser, and place the whole setup on a heating equipment. Heat the solution at reflux temperature for 30 min. After a given reflux period, the flask is allowed to cool and then the condenser is rinsed with water. The condenser is removed and the joint of the condenser and the flask are rinsed with water. All the rinses are collected in the flask.

Colorimetric titration: Add some drops of phenolphthalein indicator solution to the test solution. Titrate the solution while stirring, with 0.5N sodium hydroxide solution to the first faint pink end point that is permanent for 15 sec. Read the titrated volume to 0.1 ml accuracy.

Expression of results: Calculate the hydroxyl number in milligrams of KOH per gram of sample, with the following equation: $A = (B-C) \times F \times 28.05 \div S$ A: hydroxyl number
B: consumption amount of 0.5N sodium hydroxide solution by a blank test
F: concentration coefficient of 0.5N sodium hydroxide solution
C: consumption amount of 0.5N sodium hydroxide solution by a sample test
S: sample amount

Example 2

Measurement of the Hydroxyl Number of Commercial Nonionic Surfactant Polyoxyethylene Nonylphenyl Ether (Theoretical Hydroxyl Value of 75)

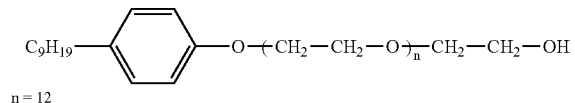

n = 12

2.0115 g of the sample was weighted in flask 1 and 2.022 g of the sample was weighted in flask 2. 5 mL esterification reagent A was pipetted into each flask used for the test portion and a blank determination. The titration result for flask 1 was 37.9 mL, and for flask 2 was 37.9 mL. The titration result for blank 1 was 43.3 mL, and for blank 2 was 43.5 mL. The average consumption amount of 0.5N sodium hydroxide aqueous solution in the blank test was 43.4 mL. The concentration coefficient of 0.5N sodium hydroxide solution was 1.003. According to the formula, the hydroxyl number of the sample in flask 1 was 76.9, the hydroxyl number of the sample in flask 2 was 76.5, and the average hydroxyl number thereof was 76.7.

Example 3

Measurement of the Hydroxyl Number of Commercial Poly(Tetramethylene Glycol) (Hydroxyl Number Given by the Maker is 107.8)

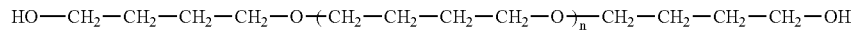

1.5514 g of the sample was weighted in flask 1 and 1.5453 g of the sample was weighted in flask 2. 5 ml esterification reagent B was pipetted into each flask used for the test portion and a blank determination. The titration result for flask 1 was 38.1 mL, and for flask 2 was 38.3 mL. The titration result for blank 1 was 44.2 mL, and for blank 2 was 44.2 mL. The average consumption amount of 0.5N sodium hydroxide solution in the blank test was 44.2 mL. The concentration coefficient of 0.5N sodium hydroxide solution was 0.979. According to the formula, the hydroxyl number of the sample in flask 1 was 108.0, the hydroxyl number of the sample in flask 2 was 104.8, and the average hydroxyl value thereof was 106.4.

Example 4

Measurement of the Hydroxyl Number of Commercial Poly(Butanediol Adipate) (Hydroxyl Number Given by the Maker is of 112.1)

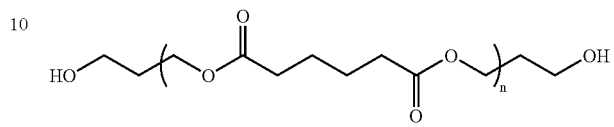

1.5230 g of the sample was weighted in flask 1 and 1.6706 g of the sample was weighted in flask 2. 5 mL esterification reagent C was pipetted into each flask used for the test portion and a blank determination. The titration result for flask 1 was 41.3 mL, and for flask 2 was 40.8 mL. The titration result for blank 1 was 47.3 mL, and for blank 2 was 47.3 mL. The average consumption amount of 0.5N sodium hydroxide solution in the blank test was 47.3 mL. The concentration coefficient of 0.5N sodium hydroxide solution was 1.0151. According to the formula, the hydroxyl number of the sample in flask 1 was 112.2, the hydroxyl number of the sample in flask 2 was 110.8 and the average hydroxyl value thereof was 111.5.

While the invention has been described by way of examples and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An esterification reagent for anhydride method to determine the hydroxyl number comprising:
   an anhydride;
   an oxometallic complex having a formula of $MO_mL_n$, wherein M is transition metals of IVB, VB, or VIB group, L is (OTf), X,

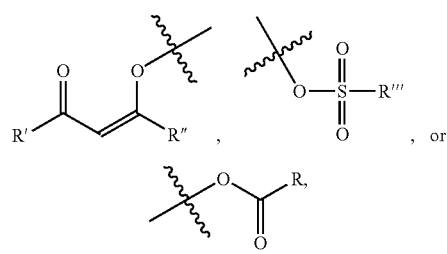

and m and n are an integer greater than or equal to 1, wherein X is halogen, and R, R', R", and R''', independently, are alkyl, aryl, or heterocyclic groups containing nitrogen, oxygen, phosphorus, or sulfur heteroatoms; and a solvent, wherein the solvent is xylene, diethylbenzene or a mixture thereof.

2. The esterification reagent as claimed in claim 1, wherein the anhydride has formula $(RCO)_2O$, wherein R is acyclic aliphatic, cyclic aliphatic or heterocyclic groups.

3. The esterification reagent as claimed in claim 2, wherein R is methyl, trifluoromethyl, monochloromethyl, ethyl, propyl or isopropyl.

4. The esterification reagent as claimed in claim 1, wherein the anhydride is acetyl anhydride, trifluoromethyl anhydride, monochloromethyl anhydride, butyl anhydride, propyl anhydride, isobutyl anhydride or a mixture thereof.

5. The esterification reagent as claimed in claim 1, wherein when M is the transition metals of IVB group, m is 1, n is 2, L comprises (OTf), X,

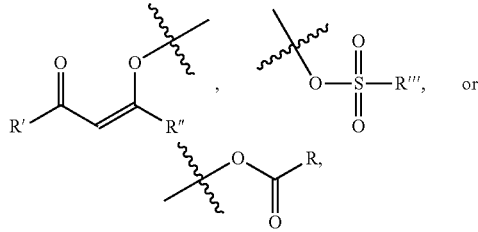

wherein X is halogen, and R, R', R", and R''', independently, are alkyl, aryl, or heterocyclic groups containing nitrogen, oxygen, phosphorus, or sulfur heteroatoms.

6. The esterification reagent as claimed in claim 1, wherein when M is the transition metals of VB group, m is 1, $L_n$ are $(OTf)_2(THF)_2$, $(OTf)_2(THF)_3$, $Cl_2(THF)_2$, $Cl_2(THF)_3$, $(OAc)_2$, $(OTs)_2$, $(OSO_2Cl_2H_2)_2$, $(SO_3\text{-alkyl})_2$, $(SO_3\text{-alkyl})_2(THF)_2$ or $(SO_3\text{-alkyl})_2(THF)_3$.

7. The esterification reagent as claimed in claim 1, wherein when M is the transition metals of VIB group, m is 1, n is 4, and L comprises X, wherein X is halogen.

8. The esterification reagent as claimed in claim 1, wherein when M is the transition metals of VIB group, m is 2, n is 2, L comprises (OTf), X,

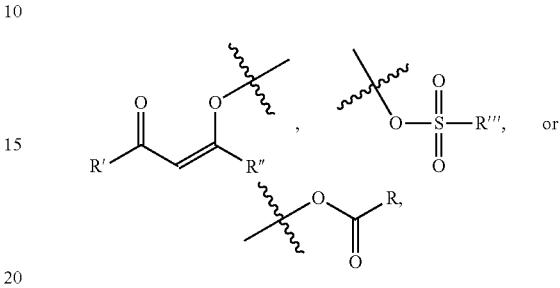

wherein X is halogen, and R, R', R", and R''', independently, are alkyl, aryl, or heterocyclic groups containing nitrogen, oxygen, phosphorus, or sulfur heteroatoms.

9. The esterification reagent as claimed in claim 1, wherein the anhydride and the oxometallic complex have a molar ratio of about 100:10-100:0.01.

10. The esterification reagent as claimed in claim 9, wherein the anhydride and the oxometallic complex have a molar ratio of about 100:5-100:0.2.

11. The esterification reagent as claimed in claim 1, wherein the solvent and the anhydride have a weight ratio of about 10:1-1:1.

* * * * *